United States Patent [19]

Koshino

[11] Patent Number: 4,821,734

[45] Date of Patent: Apr. 18, 1989

[54] SPHYGMOMANOMETER

[75] Inventor: Shinji Koshino, Shibukawa, Japan

[73] Assignee: Nihon Seimitsu Sokki Co., Ltd., Shibukawa, Japan

[21] Appl. No.: 74,204

[22] Filed: Jul. 16, 1987

[30] Foreign Application Priority Data

Apr. 21, 1987 [JP] Japan ................................ 62-98390
Apr. 21, 1987 [JP] Japan ................................ 62-98391

[51] Int. Cl.⁴ .............................................. A61B 5/02
[52] U.S. Cl. ...................................... 128/680; 128/687
[58] Field of Search ............................... 128/680–683, 128/687

[56] References Cited

U.S. PATENT DOCUMENTS

| | | | |
|---|---|---|---|
| 3,104,661 | 9/1963 | Halpern | 128/667 |
| 3,920,004 | 11/1975 | Nakayama | 128/691 |
| 4,172,450 | 10/1979 | Rogers et al. | 128/679 |
| 4,245,648 | 1/1981 | Trimmer et al. | 128/680 |
| 4,406,289 | 9/1983 | Wessiling et al. | 128/670 |
| 4,407,290 | 10/1983 | Wilber | 128/633 |
| 4,437,470 | 3/1984 | Prost | 128/679 |
| 4,566,463 | 1/1986 | Taniguchi et al. | 128/682 |
| 4,597,393 | 7/1986 | Yamakoshi et al. | 128/677 |

Primary Examiner—Francis Jaworski
Attorney, Agent, or Firm—Armstrong, Nikaido, Marmelstein & Kubovcik

[57] ABSTRACT

A non-invasive manometer comprises a bladder to be attached to an appendage such as a finger, a leg, a tail or the like in order to apply a pressure thereto. A pressure changing device changes the pressure. Two pairs of photoelectric sensors sense a change in the diameter of the blood vessel due to the applied pressure and the internal pressure of the blood vessel. Each sensor includes a light emitting unit and a photosensitive unit. At least one of the units includes a plurality of elements. The photoelectric sensors are shielded from possible external light and operated alternately in a time-divisional manner. One sensor is disposed closer to the heart than the other sensor. The output of the other sensor is used to determine the highest blood pressure while the outputs of both the sensors are compared to determine the lowest blood pressure.

4 Claims, 9 Drawing Sheets

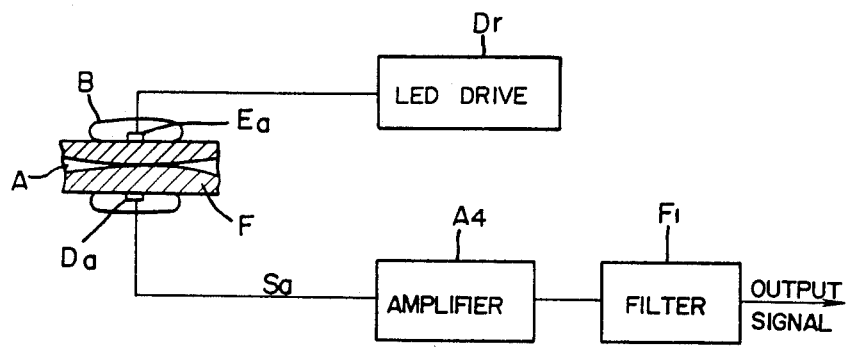
Fig.1
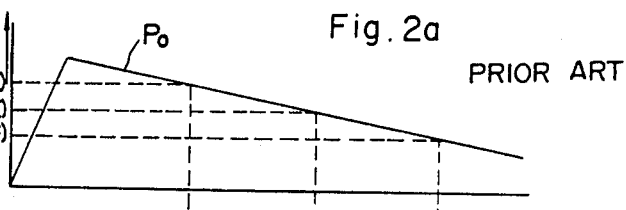
Fig.2a PRIOR ART
Fig.2b

SYSTOLIC (HIGHEST BLOOD PRESSURE)  DIASTOLIC (LOWEST BLOOD PRESSURE)

(HEART SIDE)  (PERIPHERAL SIDE)

$B_p > SYS.$ $B_p = SYS.$

----  SYSTOLIC (HIGHEST BLOOD PRESSURE)
——  DIASTOLIC (LOWEST BLOOD PRESSURE)

$B_p \leq DIA.$

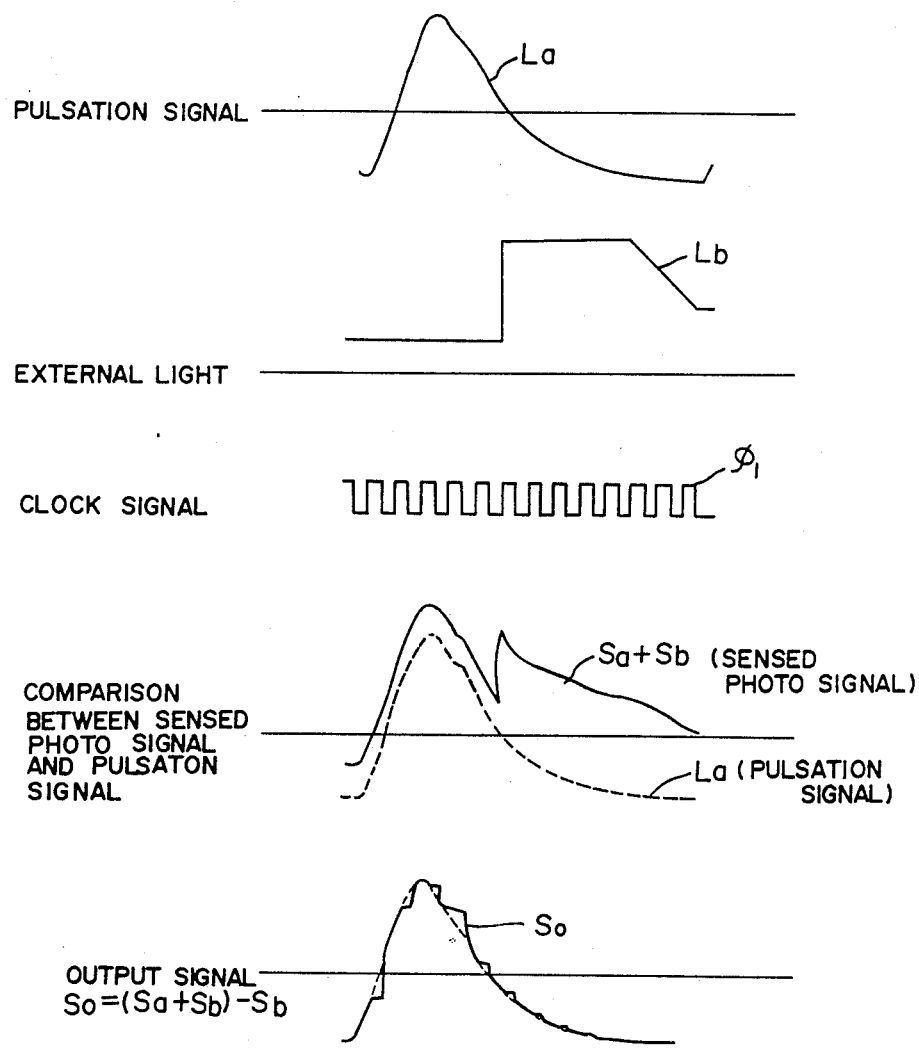

SPHYGMOMANOMETER

FIELD OF THE INVENTION

This invention relates to a sphygmomanometer. More particularly, the invention relates to a non-invasive manometer having a bladder which is mainly attached to an appendage such as a finger, an earlobe, a leg, a tail or the like. Also included is a means for applying pressure to the bladder and, hence to the blood. An optical means senses the varying diameter (volume) of the blood vessel depending upon the applied pressure and the internal pressure with the blood vessel in order to measure the blood pressure.

BACKGROUND OF THE INVENTION

Conventionally, a sphygmomanometer is applied indirectly to an appendage such as a finger or an earlobe because it is convenient. For example, U.S. Pat. No. 4,406,289 discloses the use of a servo balance technique. Another example is U.S. Pat. No. 4,597,393 which discloses a method of calculating and estimating the lowest blood pressure by observing the linearity of the blood vessel and the associated peripheral organization. Further examples are U.S. Pat. Nos. 3,104,661, 3,920,004 and 4,437,470 which disclose the use of a plurality of cuffs or sensors. Also, a sphygmomanometer may include an optical means which senses a change in the vessel diameter or volume due to the applied pressure and the internal blood vessel pressure. The optical means converts the change in blood pressure to an electric signal. Using the optical means requires the use of a cover to eliminate the influence of external light, solar light, or the like and in addition requires a place where little external light is present and/or the external light is stable. If these requirements are not considered, an error will result from the sphygmomanometry. For example, when the average blood pressure is to be measured using a signal processor shown in FIG. 1, a light emitting element drive circuit Dr activates a light emitting element Ea to emit intermittent light. The output signal from a photosensitive element Da is amplified by an amplifier A4. The intermittent components contained in the amplified signal are eliminated by a filter F1 in order to obtain an output signal having a continuous waveform. The photosensitive element Da receives a quantity of varying light which depends on a change in diameter of the blood vessel. The output signal from the photosensitive element Da is an electric signal which corresponding to the change in the diameter of the blood vessel. As shown in FIG. 2(a) if the pressure PO of a bladder B (FIG. 1) is temporarily increased higher than the highest vessel pressure and then decreased gradually, the output signal from the signal processor changes as shown in FIG. 2(b). In this case, the blood pressure corresponding to the maximum amplitude of the output signal is handled as an average blood pressure. Reference characters F and A in FIG. 1 denote a finger and a blood vessel, respectively.

In the U.S. Pat. No. 4,406,289, the device used is large in size, and requires a long time to attach the device and to adjust it, so that the device is not suitable for an application in which the measurement of blood pressure is instantaneously desired. U.S. Pat. No. 4,597,393 has several problems such as (a) producing an error due to an assumption that the elasticity of the blood vessel and its associated peripheral organization is linear, (b) producing an error due to an increase in the quantity of data due to the calculation of a small waveform area, and (c) producing an error due to reducing the quantity of data, etc. In U.S. Pat. Nos. 3,104,661, 3,920,004, and 4,437,470, it is hard, to attach two or more device elements. Pressurization cannot be allowed because it may cause an error in the measurement by a sensor on the distal side. In addition, it is impossible to determine the lowest blood pressure or a method for the determination is unclear. In the sphygmomanometer which uses an optical means, the filter cannot eliminate external light similar in frequency to the pulsating wave. Thus, all the prior art, in which light emitting elements are disposed at opposing positions on a portion of a human body to sense a change in the vessel diameter as a change in the received quantity of light which is then changed to an electric signal which is in turn processed to measure the blood pressure, will cause an error in the sphygmomanometry.

SUMMARY OF THE INVENTION

Therefore, it is an object of this invention to provide a sphygmomanometer which eliminates the above problems involving the measurement accuracy and device complexity that the prior art has, and performs sphygmomanometry with high accuracy and with a simple structure.

The means to solve the above problems according to this invention will be now described.

A first embodiment is a non-invasive manometer similar to that shown in FIG. 3 and includes (a) a pressurization means B and C attached to a finger F which applies a pressure to a finger or the like, (b) a means S for changing the pressure applied to the finger, and (c) an optical means Ea, Eb and Da, Db for sensing a change in the diameter (volume) of the blood vessel due to the applied pressure and the internal pressure of the blood vessel A. As shown in FIG. 4, either light emitting unit of the optical means may include a plurality of elements (Ea, Eb) or the photosensitive unit may include a plurality of elements (Da, Db). One of the light emitting elements (or photosensitive elements), Ea (or Da), is disposed closer to the heart than other light emitting elements (or photosensitive) elements, Eb (or Db). The plurality of elements of the optical means are operated in a time-divisional manner. The elements of the optical means are shielded from external light by shield SH. As shown in FIG. 4, comparing means Cp is provided which compares the outputs of two or more elements (Ea, Da), (Eb, Db) of the optical means positioned on the heart side and the peripheral side. The highest blood pressure is determined when the output Ss of the optical means (Eb, Db) positioned on the peripheral side appears while the lowest blood pressure is determined when the output Sd of the comparing means Cp disappears.

In a second embodiment, the sensing unit has almost the same structure as that of the first invention except that it has no shield, so that the photosensitive elements Da, Db receive external light. As shown in FIG. 8, either light emitting unit of the optical means may include a plurality of elements Ea, Eb or the photosensitive unit may include a plurality of elements Da, Db. One of the light emitting (or photosensitive) elements, Ea (or Da) is disposed closer to the heart than the other Eb (or Db). As shown in FIG. 7, the plurality of elements of the optical means are operated in a time-divisional manner and have a phase where the respective light emissions are zero. The optical signals received during the zero intervals are stored, by capacitors Ca, Cb, etc. A subtraction means (differential amplifiers A31, A32) subtracts the stored signals from the signal obtained during the light emission. Comparing means Cp compares the outputs from two or more optical means (Ea, Da), (Eb, Db) positioned on the heart side and on the peripheral side. The highest blood pressure is determined when the output Ss from the optical means (Eb, Db) positioned on the peripheral side appears while the lowest blood pressure is determined at a time when the output Sd from the comparing means Cp disappears.

A third embodiment is an additional embodiment to the first and second embodiments. Usually, the waveforms obtained from the two different positions do not coincide because of factors due to the human body as well as due to the device used. For example, the sensitivities of the light emitting diodes (as the light emitting elements) and the phototransistors (as the photosensitive elements) vary. The third embodiment is intended to attain a better coincidence of the waveform outputs from the two positions in order to determine the lowest blood pressure. As shown in FIGS. 9 and 10, one of the signals Sa', Sb' of FIGS. 4 and 8 is applied to a variable-gain amplifier A4. First, when a pressure value, for example, of 30 mm Hg, which is obviously lower than the lowest blood pressure is attained, a close-loop control circuit is temporarily operated to control the gain of the amplifier such that both the signals Sa', Sb' are equal in order to permit a highly accurate measurement of the lowest blood pressure.

A fourth embodiment is also a non-invasive manometer. As shown in FIG. 12, this device is attached to a finger F or the like. At least one of the light emitting units Ea and the photosensitive unit Da of the optical means includes at least one element. The optical means operates in a time-divisional manner. All the light emitting units have a rest or zero phase. The output from the photosensitive element Da during the rest interval (or the zero interval) of the light emitting element Ea is stored. The difference between the stored output and the output signal from the photosensitive element Da during a light emitting interval is obtained in order to eliminate the influence of external light.

BRIEF DESCRIPTION OF THE DRAWINGS

FIG. 1 is a circuit diagram of a conventional signal processor used for measurement of an average blood pressure;

FIG. 2 illustrates sphygmomanometry;

FIG. 13 illustrates the measurement of respective signals in FIG. 12.

DETAILED DESCRIPTION OF THE PREFERRED EMBODIMENT

Figure 3:
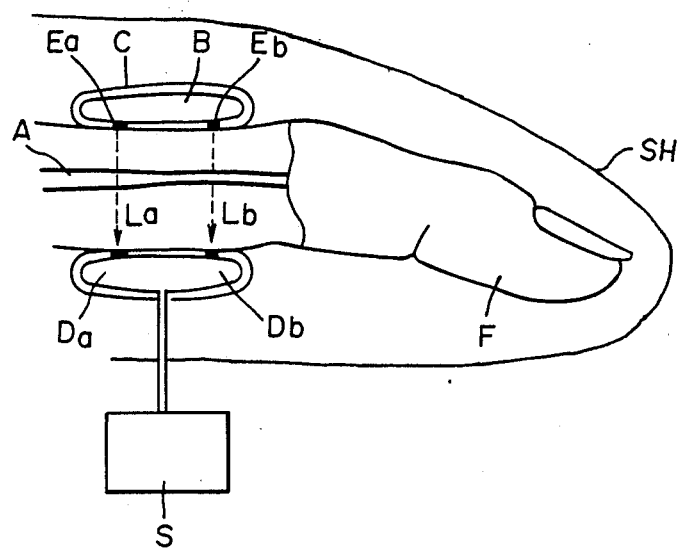
FIG. 3 is a cross-sectional view of a part of a sensor of the sphygmomanometer according to this invention.

FIG. 3 is a partially cross-sectional view showing the structure of a sensor in a first and second embodiment of the invention. Reference character F denotes a finger, the left half of which is shown in a cross-sectional view. Reference character A denotes an artery within the finger. A bladder B applies air pressure to the finger. A cuff C limits the expansion of the bladder. A pressure changing device S controls the air pressure within the bladder. Light emitting elements Ea, Eb emit, for example, infrared rays. Photosensitive elements Da, Db are, for example, a phototransistor. In FIG. 3, light emitting element Ea is disposed opposite to the photosensitive element Da so that light from element Ea reaches the photosensitive element through the finger (including the artery). For example, if the bladder B is opaque, they are disposed between the finger and the bladder. If the bladder is transparent, they may be disposed on the inner surface of the bladder or between the bladder and the cuff C. The light emitting element Eb and the photosensitive element Db are similarly disposed opposite to each other. It is to be noted that the elements Ea and Da are disposed closer to the heart rather than at the center of the bladder B, while the elements, Eb and Db are disposed on the peripheral side rather than at the center of the bladder. The quantity of light transmitted from the light emitting element Ea to the photosensitive element Da is influenced by a change in the volume of the artery (blood vessel) A due to a change in the internal blood pressure. Similarly, the photosensitive element Db outputs a signal representing the change in the volume of the artery due to the light Lb from the light emitting element Eb. In this case, if the light emitting elements and the photosensitive elements receive external light components, an error may be involved in the measurement. In order to avoid this, the first invention protects the optical means from external light using a shielding means SH. For example, a pair of gloves may be used. The second invention electrically eliminates external light without using the shielding means SH.

First, the first embodiment will be described as follows:

Light emitting elements Ea, Eb emit light alternately using a two-phase clock so that their emission intervals do not overlap. The photosensitive elements Da, Db are turned on synchronously with the light emission clock to receive the light La, Lb from the corresponding opposing light emitting elements Ea, Eb. A clock frequency of 60 or as high as the maximum expected pulsation rate is used as the light emitting on-off frequency in order to obtain a correct pulsation waveform.

Figure 4:
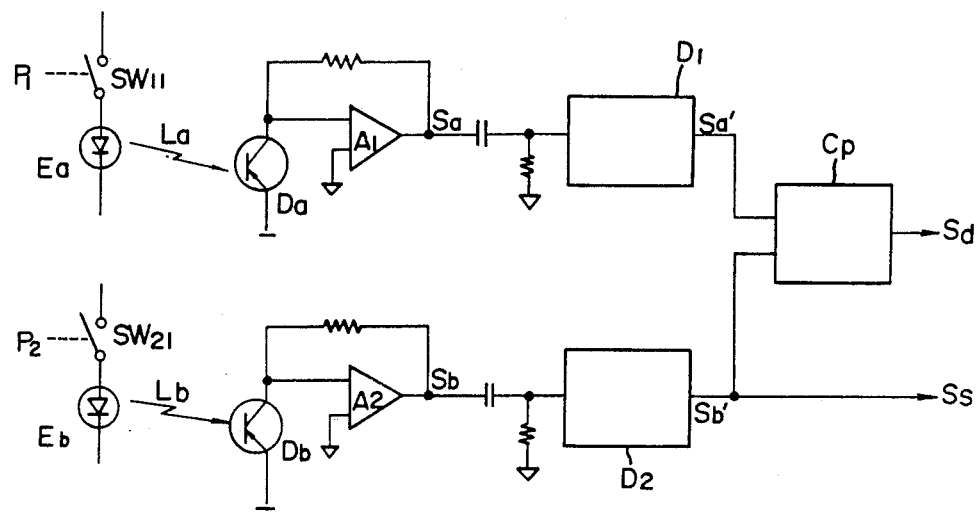
FIG. 4 is a circuit diagram of a signal processor used in the method shown in FIG. 3.

The operation of the first embodiment will now be described using the circuit of FIG. 4.

First, the light emitting element Ea emits light at a phase P1 via a switch SW11. The photosensitive element Da is shielded from external light, so that it receives only light La from the light emitting element Ea. The light La is changed by the photosensitive element Da into a voltage signal which is then amplified by an amplifier A1 into a signal Sa.

Similarly, at a phase P2, light emitting element Eb emits light Lb which is received by the photosensitive element Db and changed into a voltage signal Sb. These signal voltages Sa, Sb are detected by detectors D1, D2, which eliminate the clock components as the carriers and which output signals Sa', Sb' corresponding to changes in the volume of the blood vessel. Comparator Cp compares signals Sa', Sb' to provide a difference signal Sd. When the signals Sa', Sb' coincide in waveform and amplitude, the comparator produces a zero output.

Figure 6:
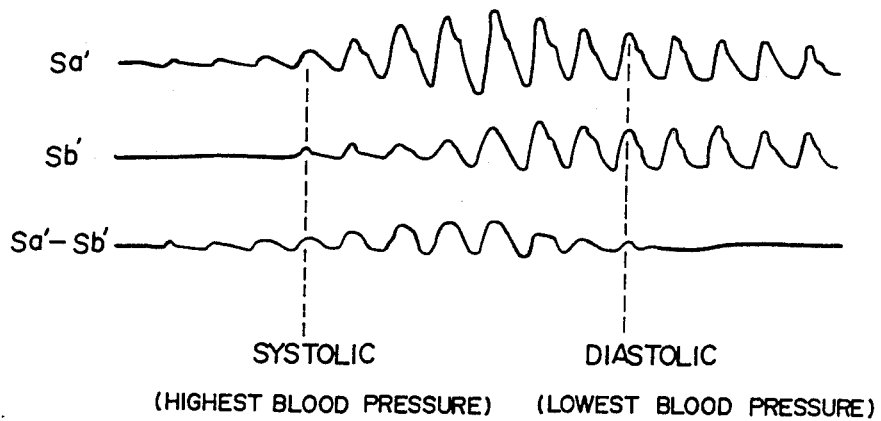
FIGS. 5 and 6 illustrate a blood vessel and blood flow for determining the highest and lowest blood pressures.

The determination of the highest and lowest blood pressures SYSTOLIC and DIASTOLIC will be described with respect to FIGS. 5 and 6.

Figure 5A:
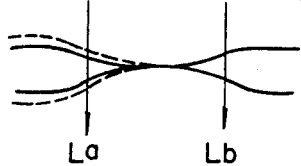
Figure 5B:
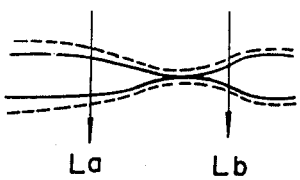
Figure 5C:
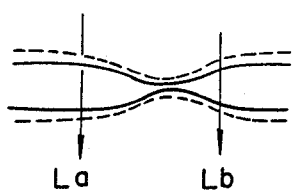

First, the bladder B is pressurized temporarily higher than the highest blood pressure by pressure changing means S. The bladder is then depressurized gradually by pressure changing means S. At this time, the volume of the blood vessel changes are shown in FIG. 5(a), 5(b), 5(c) and the signals Sa', Sb' change, as shown in FIG. 6. Namely, when the bladder pressure is higher than the highest blood pressure, the blood vessel remains closed and no blood flows (see FIG. 5(a)). Therefore, the volume of the blood vessel on the peripheral side does not change and no change due to light Lb occurs, while the volume of the blood vessel on the heart side does change and hence light La changes. Namely, no signal Sb' is produced but signal Sa' is produced (see the left portion of FIG. 6).

When the bladder pressure decreases slightly below the highest blood pressure, the blood vessel opens only during the interval in which the internal pressure is higher than the external pressure to produce a flow of blood (see FIG. 5(b)). This causes a quantity of light Lb to change to thereby produce a signal Sb' (see SYSTOLIC in FIG. 6).

When the bladder pressure decreases below the lowest blood pressure, there is no interval in which the blood vessel closes (see FIG. 5(c)), so that changes for the light La and Lb are equal and hence signals Sa', Sb' are equal. Comparator Cp compares signals Sa', Sb' to output the difference Sd, so that the difference becomes zero at the lowest blood pressure (see DIASTOLIC at the lower part of FIG. 6).

In this way, the highest blood pressure can be determined at a point where signal Sb' appears while the lowest blood pressure can be determined from a point where the difference signal Sd between signals Sa' and Sb' disappears.

Figure 7:
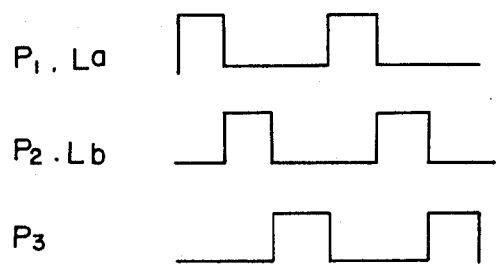
FIG. 7 illustrates the phase relationship of light emission and extinction by the light emitting elements.

Now, the second embodiment of the invention will be described as follows:

The sensor of FIG. 3 has quite the same structure as that of the first embodiment but is not externally shielded by shield means SH. Therefore, the photosensitive elements Da, Db receive external light. The light emitting elements Ea, Eb emit light by a multi-phase clock so that their respective light emitting intervals do not overlap. The photosensitive elements Da, Db are switched ON or OFF simultaneously with the light emission clock. As shown in FIG. 7, light emitting element Ea emits light at phase P1, light emitting elements Eb emit light at phase P2 and none of the elements Ea, Eb emit light at phase P3. A clock frequency of sixty or as high as the highest expected pulsation rate is used as the light emitting on-off frequency in order to reproduce a correct pulsation waveform. At phase P3, where neither element Ea or Eb emit light, the photosensitive elements Da, Db receive external light Lc.

The peripheral light (lamp light or solar light) illuminates the finger F and is scattered at each end of the cuff C by finger F and arrives at the photosensitive elements Da, Db. This light is designated Lc.

Figure 8:
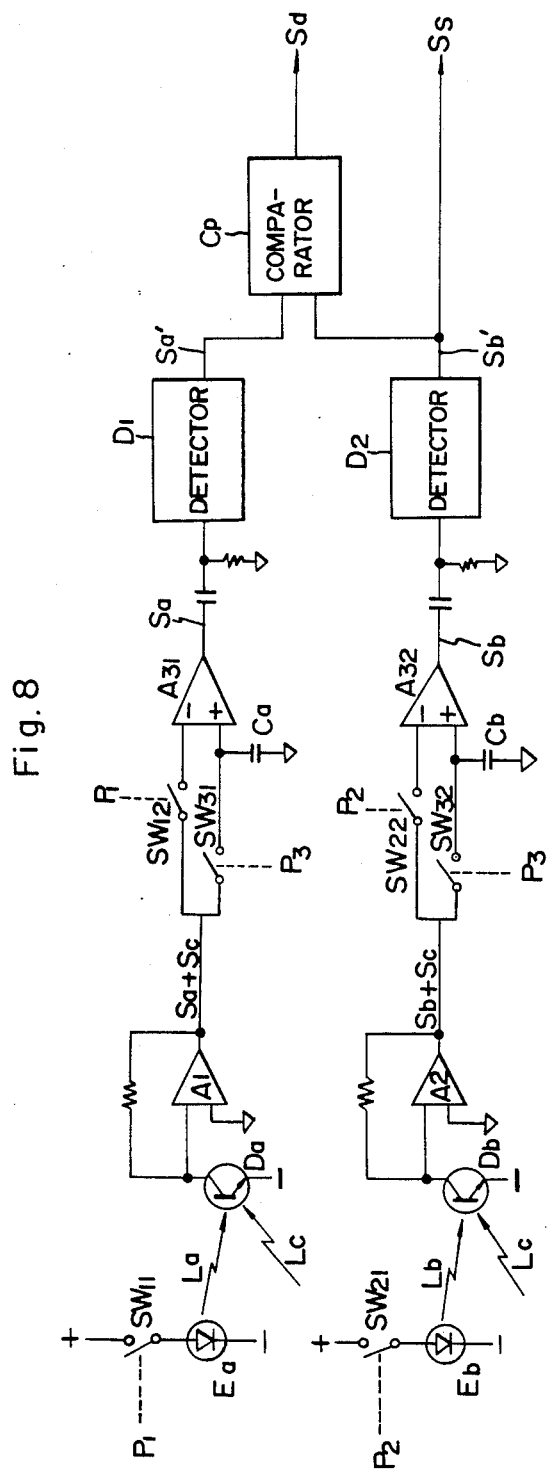
FIG. 8 is a circuit diagram of a signal processor showing another embodiment of this invention.

The operation of the second embodiment will now be described with reference to FIG. 8. The signal obtained by photosensitive element Da is amplified by amplifier Al and delivered via switch SW12 to a differential amplifier A31. The operation of switches SW11, SW12 and differential amplifier A31 will be described. At phase P1, light emitting element Ea emits light via switch SW11. Photosensitive element Da receives light La from light emitting element Ea as well as external light Lc. Namely, it receives light La+Lc at phase P1. This light is changed into a voltage signal which is amplified by amplifier A1 to a signal Sa+Sc.

At phase P2, similarly, light emitting element Eb emits light and photosensitive element Db receives light Lb+Lc which is changed into a voltage signal Sb+Sc. At phase P3, element Db receives only light Lc and the signal Sc is connected via switches SW31, SW32 to non-inverting inputs of the two amplifiers A31, A32. The signal voltages are held on the non-inverting input sides even after completion of phase P3 by capacitors Ca, Cb which are connected at the non-inverting inputs. At phase P1, the signal Sa +Sc is connected to non-inverting input of amplifier A31 and the signal Sc is connected via switch SW31 to the non-inverting input of amplifier A31. Therefore, the differential amplifier A31 outputs the difference between the two inputs, namely, $Sc-(Sa+Sc) = -Sa$. Similarly, at phase P2, the differential amplifier A32 outputs a signal $Sc-(Sb+Sc) = -Sb$.

As described above, the differential amplifiers A31, A32 output signal components free from signal Sc due to external light. The signal voltages Sa, Sb are detected by detectors D1, D2. Namely, the carrier, including a clock component, is eliminated from the signal voltages Sa, Sb to provide signals Sa', Sb' corresponding to the changes in the volume of the blood vessel. Comparator Cp, which is similar to that in the first embodiment, signals Sa' and Sb' in order to output the difference signal Sd. When both signals Sa' and Sb' coincide in waveform and amplitude, the output of the comparator Cp is zero.

In the above arrangement, the determination of the highest blood pressure SYSTOLIC and the lowest blood pressure DIASTOLIC is the same as in the first embodiment and a description therefore will be omitted.

According to the above method, the lowest blood pressure can be highly accurately measured. However, this method may be influenced by variations in the elements used or caused by a living body whose lowest blood pressure is to be measured. A third embodiment will be described in which, the waveform outputs from two positions coincide in order to determine the lowest blood pressure by elimination the influence caused by a living body, etc.

Figure 9:
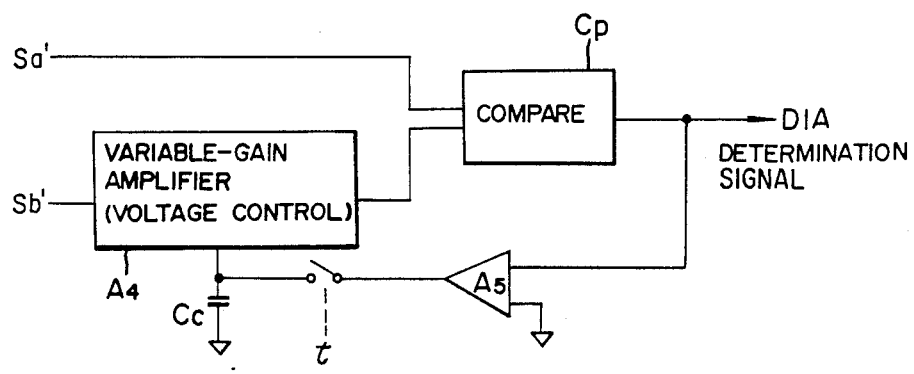
FIG. 9 is a circuit diagram of an additional circuit for improvement to this invention.
Figure 10:
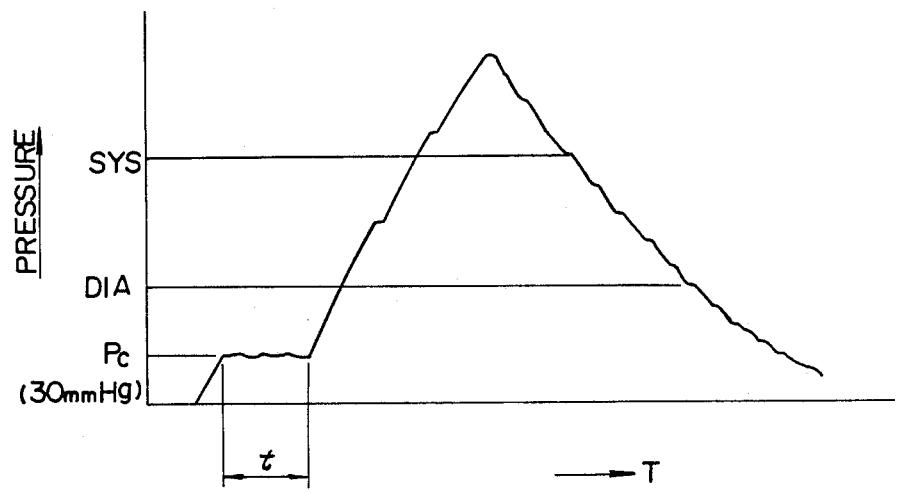
FIG. 10 illustrates the operation of the circuit of FIG. 9.

FIG. 9 shows the circuit diagram of the third embodiment. FIG. 10 illustrates the operation of the circuit of FIG. 9. In FIGS. 9 and 10, signals Sa', Sb' correspond to a change in the volume of the blood vessel in FIG. 1. Either one of the signals Sa', Sb' is input via a variable-gain amplifier A4 to comparator Cp of FIG. 4. The gain of amplifier A4 is adjusted so that both signals are equal in amplitude. Namely, a closed-loop control circuit is temporarily operated in which the output from comparator Cp is delivered via amplifier A5 to the variable-gain amplifier A4.

The operation of the closed-loop control is performed when a pressure value Pc (for example, 30 mmHg) is attained which is obviously lower than the lowest blood pressure at the beginning of pressurization and depressurization of the sphygmomanometer, as shown in FIG. 10. Pressurization is first stopped for a time t to maintain a constant pressure.

The reason for maintaining a constant pressure is that the signals Sa', Sb' must be first equalized below the lowest pressure. Namely, the output from comparator Cp must be zero. However, if signals Sa', Sb' are not equal, the output from comparator Cp will not be zero, in which case the output from comparator is applied to the variable-gain amplifier A4 and the gain of the amplifier is controlled so that the output from the comparator will be zero. This controlled value is held until the measurement ends by storing the value, for example, in a capacitor Cc.

As soon as the controlled value is stored, pressurization is again performed to a value higher than the highest blood pressure and then a measurement is taken as mentioned above. Instead of the variable-gain amplifier, for example, an amplifier may be used which has a plurality of resistors and a switch to select one of the resistors to determine a desired gain. The switch may be controlled by a digital signal. This system can absorb any disruptive factors caused by the living body or by the device, for example, variations in the sensitivity of the LEDs and phototransistors.

The concept of equalizing outputs from two sets of optical systems may be realized by other means, one example of which will be described below.

Figure 11:
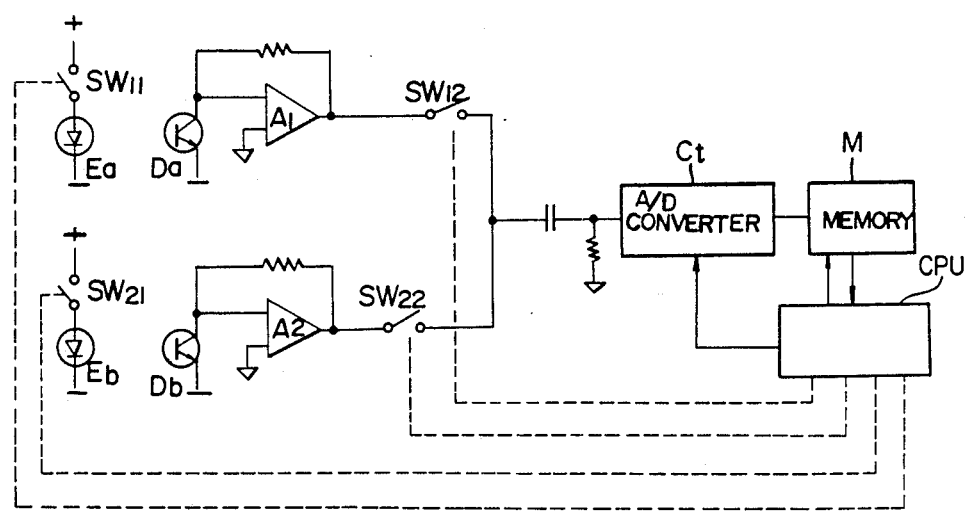
FIG. 11 is a circuit diagram of a signal processor showing another embodiment of this invention.

As shown in FIG. 11, part of an analog means may be replaced with a digital means. The optical means used is the same as those described with reference to FIGS. 4 and 8, but without the differential amplifiers A31, A32; detector circuits D1, D2 and comparator Cp. Instead, the functions of these circuits are performed digitally.

More particularly, the respective outputs of the two sets of optical means are converted by an analog to digital (A/D) converter Ct and are stored as a digital variable in a memory M. Of course, the outputs from the optical means are stored separately at a phase P where no light is emitted from the light emitting elements. Differential amplifiers A31, A32 function to eliminate the influence of external light by subtracting a signal at phase P3 from a signal at phase P1. This similarly occurs at phase P2. The respective signals are stored as a digital quantity. A central processing unit CPU determines the difference by performing a digital subtraction. Detectors D1,D2 function to extract frequency components of the pulsation wave by eliminating the clock component (the carrier). The A/D convertor is operated synchronously with a clock signal, and the clock components are automatically eliminated. Also, comparator Cp may be implemented as a digital device.

This system saves several analog parts but requires many memory elements.

Figure 12:
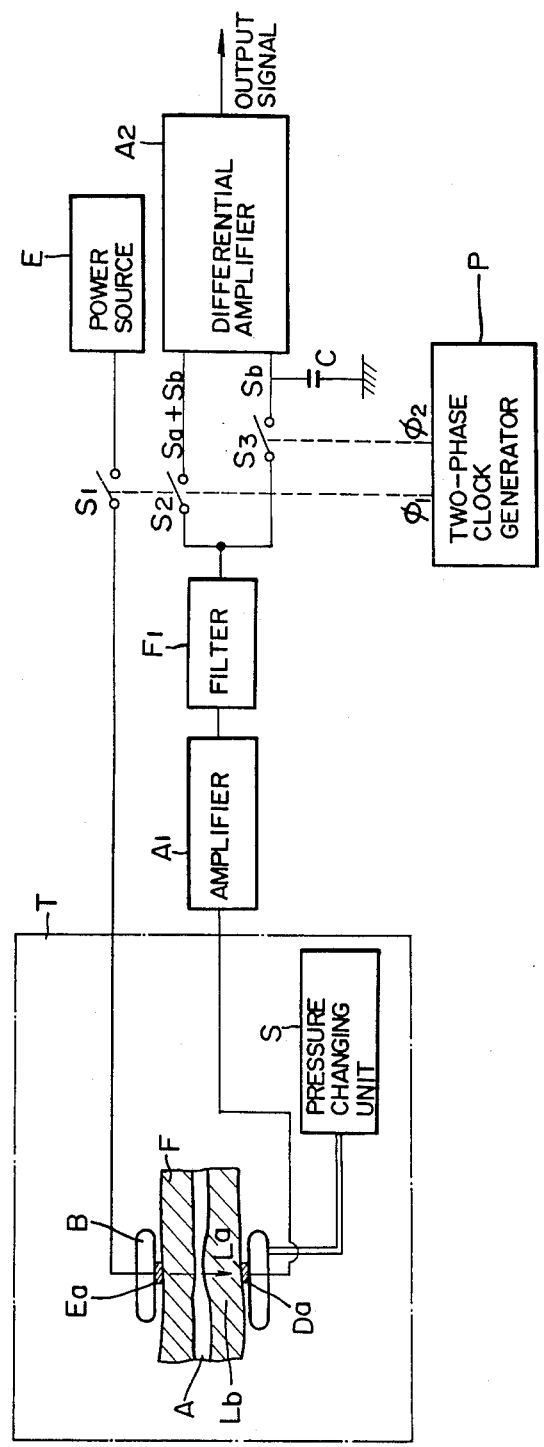
FIG. 12 is a circuit diagram showing another embodiment of the sphygmomanometer according to this invention.

A fourth embodiment will now be described with reference to FIG. 12 which is an example of a circuit used where an average blood pressure is measured using a set of optical means. The manometer used includes a sensor T which measures the blood pressure in a non-invasive manner. The sensor is attached to an appendage such as a finger F, an earlobe or the like. A pressure changing unit S changes the pressure applied to the finger, the earlobe or the like. An optical means senses a change in the diameter or volume of the blood vessel due to the applied pressure and the internal pressure in the blood vessel A. The optical means includes a light emitting element Ea and photosensitive element Da. Use of one pair of light emitting elements Ea and photosensitive element Da of the optical means is not important. At least one of the light emitting unit Ea and the photosensitive unit Da may include a plurality of elements. The optical means is driven by a two-phase clock generator P in a time-divisional manner and has a phase where all the light emitting elements stop emission. Reference character La denotes light from light emitting diode Ea through the finger to the corresponding photosensitive element Da. Reference numeral Lb denotes external light entering the finger and arriving at photosensitive element Da. Reference characters S1, S2, S3 denote electric switches in which switches S1, S2 are controlled by a clock $\phi 1$ from the two-phase clock generator P while switch S3 is controlled by a clock $\phi 2$. Clocks $\phi 1$, $\phi 2$ are alternating outputs from the two-phase clock generator P. Reference character C denotes a capacitor which holds a voltage whether switch S3 is OFF or ON. Differential amplifier A2 outputs a signal corresponding to the difference between the two input signals.

When switches S1, S2 are turned on, a power source E lights the light emitting element Ea. At this time, photosensitive element Da receives the sum of light La from light emitting element Ea and external light Lb to output a signal which is amplified by amplifier A1 and output via a filter F1 as a signal Sa+Sb to one terminal of differential amplifier A2. When switch S3 is then turned ON, photosensitive element Da receives only external light Lb and outputs a signal Sb to the other terminal of differential amplifier A2. Thus, differential amplifier A2 outputs the difference between the two inputs, namely, $SO = (Sa + Sb) - Sb = Sa$ which includes a pulsation wave component free from external light Lb component. FIG. 13 shows the waveform of these signals in which the clock output $\phi 1$ is roughly depicted. The clock frequency is in fact higher than the pulsation frequency. For example, the clock frequency may be 100 times higher than the pulsation frequency so that the original waveform can be reproduced by filter F1.

In the conventional manometer which uses an optical system with one set of elements, it is difficult to obtain the value of the lowest blood pressure. Therefore, the conventional manometer calculated the highest blood pressure as well as the average blood pressure. In order to obtain the average blood pressure with higher accuracy, the optical means must be disposed near the center of the bladder. In the present invention, this means obtaining an intermediate signal between signals Sa' and Sb' corresponding to a change in the volume of the blood vessel, so that obviously the highest blood pressure will be measured as a value higher than the actual highest pressure. Since the distance between the two sets of optical means is short, there are few differences in physical characteristics between the blood vessels and between the skin portions and also few differences in the phase between the signals. Since the same pressure is applied to both of the optical systems, the outputs from the optical systems highly accurately coincide at the lowest blood pressure. The time-divisional light emission serves to decrease power consumption. Providing a phase P3 where no light emitting elements emit light and prolonging the interval of phase P3 serve to further decrease the power consumption.

As described above in detail, a manometer according to this invention is capable of measuring the highest blood pressure with higher accuracy than the prior art in which a set of optical means is provided at the center portion where pressure is applied. In the present invention, distance between two sets of optical means is short, which permits measurement of the lowest blood pressure with higher accuracy than the method in which sensors are disposed at distant positions. Turning on the light emitting elements in a time-divisional manner eliminates the entrance of external light and eliminates mutual interference between the two sets of optical means, and reduces power consumption.

From the foregoing description of the preferred embodiments of the invention, it will be apparent that many modifications may be made therein. It should be understood that these embodiments are intended as one example of the invention only, and that the invention is not limited, thereto. Therefore, it should be understood that the appended claims are intended to cover all modifications that fall within the true spirit and scope of the invention.

I claim:

1. A non-invasive manometer comprising:
   pressure means attached to an appendage for applying a pressure thereto;
   pressure changing means for changing the pressure applied to said appendage;
   optical means for sensing a change in a blood vessel of the appendage due to the applied pressure of the pressure means and internal pressure of the blood vessel caused by beating of a heart, the optical means including a light emitting unit and a photosensitive unit, the units including at least first and second pairs of light emitting elements and photosensitive elements;
   shielding means for shielding the optical means from light external to the optical means;
   clock means for operating the light emitting and photosensitive units alternately in a time-divisional manner;
   said first pair of light emitting element and photosensitive element being disposed on said appendage closer to said heart than said second pair of light emitting element and photosensitive element, said second pair of light emitting element and photosensitive element, which is disposed on a peripheral side, for determining a systolic blood pressure; and
   comparison means for comprising outputs from two or more pairs of elements of the optical means, which are disposed closer to said heart and disposed on the peripheral side, to determine a diastolic pressure when said outputs coincide.

2. A non-invasive manometer comprising:
   pressure means attached to an appendage for applying a pressure thereto;
   pressure changing means for changing the pressure applied to said appendage;
   optical means for sensing a change in a blood vessel of the appendage due to the applied pressure from the pressure means and internal pressure of the blood vessel caused by beatings of a heart, the optical means including a light emitting unit and a photosensitive unit, the units including at least first and second pairs of light emitting elements and photosensitive elements;
   shielding means for shielding the optical means from light external to the optical means;
   clock means for operating the light emitting and photosensitive units alternately in a time-divisional manner;
   phase means for providing a phase in which all emissions of light, from said light emitting unit, stop;
   storage means for storing the signal received during the phase when all light emissions stop;
   subtraction means for subtracting the stored signal from a signal obtain during light emission;
   said first pair of light emitting element and photosensitive element being disposed on said appendage closer to said heart than said second pair of light emitting element and photosensitive element, said second pair of light emitting element and photosensitive element, which is disposed on a peripheral side, for determining a systolic blood pressure; and
   comparison means for comparing outputs from two or more pairs of elements of the optical means, which are disposed closer to the heart and disposed on the peripheral side, to determine a diastolic pressure when said outputs coincide.

3. A non-invasive manometer comprising:
   pressure means for attachment to an appendage for applying a pressure thereto;
   pressure changing means for changing the pressure applied to said appendage;
   optical means for sensing a change in a blood vessel of the appendage due to the applied pressure from the pressure means and internal pressure of the blood vessel caused by beating of a heart, the optical means including a light emitting unit and a photosensitive unit, the unit including at least first and second pairs of light emitting elements and photosensitive elements;
   said first pair of light emitting element and photosensitive element being disposed on the appendage closer to the heart than said second pair of light emitting element and photosensitive element, said second pair of light emitting element and photosensitive element, which are disposed on a peripheral side, for determining a systolic blood pressure;
   comparison means for comparing outputs from two or more pairs of elements of the optical means, which are disposed closer to said heart and disposed on the peripheral side, to determine a diastolic pressure when said outputs coincide;
   a variable gain amplifier for applying one or more signals from the elements of the optical means;
   stopping means for stopping application of a pressure at a value lower than an average diastolic blood pressure at a beginning of pressurization and depressurization process; and
   means for maintaining the pressure value substantially constant while controlling gain of the variable-gain amplifier so that the outputs from the two or more elements of the optical means are equalized in order to measure the diastolic blood pressure.

4. A non-invasive manometer comprising:
   pressure means for attachment to an appendage for applying a pressure thereto;
   pressure changing means for changing the pressure applied to said appendage;
   optical means for sensing a change in a blood vessel of the appendage due to the applied pressure and internal pressure of the blood vessel, the optical means including a light emitting unit and a photosensitive unit;

clock means for operating the optical means in a time-divisional manner;

phase means for providing a phase in which the light emitting unit stops emission;

storage means for storing output from the photosensitive unit during a phase when the light emitting unit does not emit light; and means for obtaining a difference between an output signal from the photosensitive unit and a stored signal to eliminate influence of light which is external to the optical means.

* * * * *